US005693814A

United States Patent [19]

Kimura et al.

[11] Patent Number: 5,693,814
[45] Date of Patent: Dec. 2, 1997

[54] CRYSTALS OF ANTIMICROBIAL COMPOUND

[75] Inventors: Youichi Kimura; Katsuhiro Kawakami; Norimasa Mikata; Keiji Uchiyama; Tazuo Uemura; Yusuke Yukimoto, all of Tokyo, Japan

[73] Assignee: Daiichi Pharmaceutical Co., Ltd., Tokyo, Japan

[21] Appl. No.: 303,812

[22] Filed: Sep. 12, 1994

[30] Foreign Application Priority Data

Sep. 10, 1993 [JP] Japan ................. 5-225380

[51] Int. Cl.$^6$ .............. C07D 215/18; C07D 215/38; C07D 215/56
[52] U.S. Cl. ............. 546/156; 546/157; 546/159; 514/312
[58] Field of Search ............ 514/312; 546/156, 546/157, 159

[56] References Cited

U.S. PATENT DOCUMENTS

| | | | |
|---|---|---|---|
| 5,017,581 | 5/1991 | Nishitani et al. | 514/300 |
| 5,409,933 | 4/1995 | Kim et al. | 514/254 |

FOREIGN PATENT DOCUMENTS

| | | |
|---|---|---|
| 91110833.5 | 2/1992 | China . |
| 1062906 | 7/1992 | China . |
| 0206283A2 | 12/1986 | European Pat. Off. . |
| 0341493 | 11/1989 | European Pat. Off. . |
| 0341493A2 | 11/1989 | European Pat. Off. . |
| 0444678 | 9/1991 | European Pat. Off. . |
| 0444678A1 | 9/1991 | European Pat. Off. . |
| 203 719 | 9/1982 | Germany . |

OTHER PUBLICATIONS

Hendrickson, *Organic Chemistry*, third edition, pp. 10 and 452–456, 1970.
An English specification which corresponds to German Patent Application DD-A-203 719, 1982.
Chemical Abstracts, vol. 119, No. 11, 13 Sep. 1993, Columbus, Oh, Y. Yukimoto et al., "Process for preparing 8-chloroquinolone derivatives" —Abstract No. 117137s, p. 919.
CN-A 1 062 906 22 Jul. 1992.

*Primary Examiner*—C. Warren Ivy
*Assistant Examiner*—D. Margaret M. Mach
*Attorney, Agent, or Firm*—Sughrue, Mion, Zinn, Macpeak & Seas, PLLC

[57] ABSTRACT

A method for selectively obtaining any one of an anhydrate, a ½ hydrate, a 1 hydrate, and a 3/2 hydrate of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid is disclosed, comprising treating the compound in an aqueous solvent or water or recrystallizing the compound from an aqueous solvent or water.

31 Claims, 4 Drawing Sheets

CRYSTALS OF ANTIMICROBIAL COMPOUND

FIELD OF THE INVENTION

This invention relates to crystals containing water of crystallization (hereinafter referred to as hydrate form or hydrate, simply), and crystals without water of crystallization (hereinafter referred to as anhydrate form or anhydrate, simply), and to a method for selectively preparing these crystals, and further to pharmaceutical preparations containing such a crystalline form.

BACKGROUND OF THE INVENTION

A quinolone derivative represented by formula (I):

i.e., 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid (hereinafter referred to as compound (I)), has high antimicrobial activity with excellent safety (cf. EP-A-0 341 493 or JP-A-2-231475; the term "JP-A" as used herein means an "unexamined published Japanese Patent Application") and is expected to be an excellent synthetic antimicrobial agent.

It was found that the compound (I) can exist in the form of several kinds of hydrate forms other than a ¼ (0.25) hydrate, such as a ½ (0.5) hydrate (i.e., hemihydrate), a 1 hydrate (i.e., monohydrate), and a 3/2 (1.5) hydrate (i.e., sesquihydrate). It was also found that an anhydrate form exists in addition to these hydrates.

Hydrate form of compound (I) include plural types of crystals having different number of crystal water molecules. Depending on the conditions for crystallization or recrystallization, plural types of hydrates are formed in the resulting crystals, and such crystals are unsuitable as a bulk material for solid pharmaceutical preparations.

SUMMARY OF THE INVENTION

As a result of extensive investigations, the present inventors have found that it is possible to selectively prepare crystals of specific hydrate or anhydrate of compound (I) by controlling the conditions for crystallization or recrystallization. The present invention was completed based on this finding.

Accordingly, the present invention relates to a method for selectively obtaining a 3/2 hydrate of compound (I) which comprises treating 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid in an aqueous solvent or water or recrystallizing compound (I) from an aqueous solvent or water.

The present invention relates to a method for selectively obtaining a 3/2 hydrate of compound (I) which comprises treating 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid in an aqueous solvent or water.

The present invention relates to a method for selectively obtaining a 3/2 hydrate of compound (I) which comprises recrystallizing 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid from an aqueous solvent or water.

The present invention also relates to the aforementioned methods, wherein the aqueous solvent is an aqueous ethanol containing ammonia.

The present invention also relates to 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid 3/2 hydrate.

The present invention also relates to 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid anhydrate.

The present invention also relates to a crystal of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid 3/2 hydrate which substantially has the following X-ray diffraction characteristics.

| d Value (lattice spacings) (Å) | Relative Intensity |
|---|---|
| 11.47 | Weak |
| 10.49 | Strong |
| 9.69 | Weak |
| 7.12 | Extremely Weak |
| 6.87 | Strong |
| 6.23 | Strong |
| 5.68 | Weak |
| 5.25 | Strong |
| 4.90 | Extremely Strong |
| 4.71 | Extremely Weak |
| 4.61 | Weak |
| 4.25 | Weak |
| 4.15 | Extremely Weak |
| 4.01 | Strong |
| 3.85 | Extremely Weak |
| 3.80 | Extremely Weak |
| 3.74 | Extremely Weak |
| 3.69 | Weak |
| 3.58 | Weak |
| 3.50 | Weak |
| 3.46 | Weak |
| 3.39 | Weak |
| 3.34 | Weak |
| 3.29 | Weak |
| 3.17 | Weak |

The present invention further relates to pharmaceutical preparations containing the single hydrate or anhydrate mentioned above.

The present invention relates to an antibacterial agent comprising as an active ingredient a therapeutically effective amount of 7-[7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid 3/2 hydrate.

The present invention also relates to an antibacterial agent comprising as an active ingredient a therapeutically effective amount of 7-[7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid 3/2 hydrate which substantially has the following X-ray diffraction characteristics.

| d Value (lattice spacings) (Å) | Relative Intensity |
|---|---|
| 11.47 | Weak |
| 10.49 | Strong |
| 9.69 | Weak |
| 7.12 | Extremely Weak |
| 6.87 | Strong |
| 6.23 | Strong |
| 5.68 | Weak |
| 5.25 | Strong |
| 4.90 | Extremely Strong |
| 4.71 | Extremely Weak |
| 4.61 | Weak |
| 4.25 | Weak |
| 4.15 | Extremely Weak |
| 4.01 | Strong |
| 3.85 | Extremely Weak |
| 3.80 | Extremely Weak |
| 3.74 | Extremely Weak |
| 3.69 | Weak |
| 3.58 | Weak |
| 3.50 | Weak |
| 3.46 | Weak |
| 3.39 | Weak |
| 3.34 | Weak |
| 3.29 | Weak |
| 3.17 | Weak |

Moreover, the present invention relates to a method for treating bacterial infections which comprises administering a therapeutically effective amount of 7-[7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid ½ hydrate.

The present invention also relates to a method for treating bacterial infections which comprises administering a therapeutically effective amount of 7-[7-(S)-amino-5-azaspiro[2.4]heptan-5-yl]-8-chloro-6-fluoro-1-[(1R,2S)-2-fluorocyclopropyl]-4-oxo-1,4-dihydro-quinoline-3-carboxylic acid ½ hydrate which substantially has the following X-ray diffraction characteristics.

| d Value (lattice spacings) (Å) | Relative Intensity |
|---|---|
| 11.47 | Weak |
| 10.49 | Strong |
| 9.69 | Weak |
| 7.12 | Extremely Weak |
| 6.87 | Strong |
| 6.23 | Strong |
| 5.68 | Weak |
| 5.25 | Strong |
| 4.90 | Extremely Strong |
| 4.71 | Extremely Weak |
| 4.61 | Weak |
| 4.25 | Weak |
| 4.15 | Extremely Weak |
| 4.01 | Strong |
| 3.85 | Extremely Weak |
| 3.80 | Extremely Weak |
| 3.74 | Extremely Weak |
| 3.69 | Weak |
| 3.58 | Weak |
| 3.50 | Weak |
| 3.46 | Weak |
| 3.39 | Weak |
| 3.34 | Weak |
| 3.29 | Weak |
| 3.17 | Weak |

DETAILED DESCRIPTION OF THE INVENTION

First of all, the inventors studied crystals of compound (I) and, as a result, found that there are crystals of anhydrate form and hydrate forms and that the hydrate forms include a ½ hydrate, a 1 hydrate and a ³⁄₂ hydrate in addition to ¼ hydrate. From the viewpoint of the industrial production of the crystal, the ³⁄₂ hydrate is preferred because of its physicochemical stability as well as yield and ease in setting of production condition when a bulk material for pharmaceuticals is produced. On the other hand, the anhydrate is good in dissolution rate itself and from a tablet.

Figure 1:
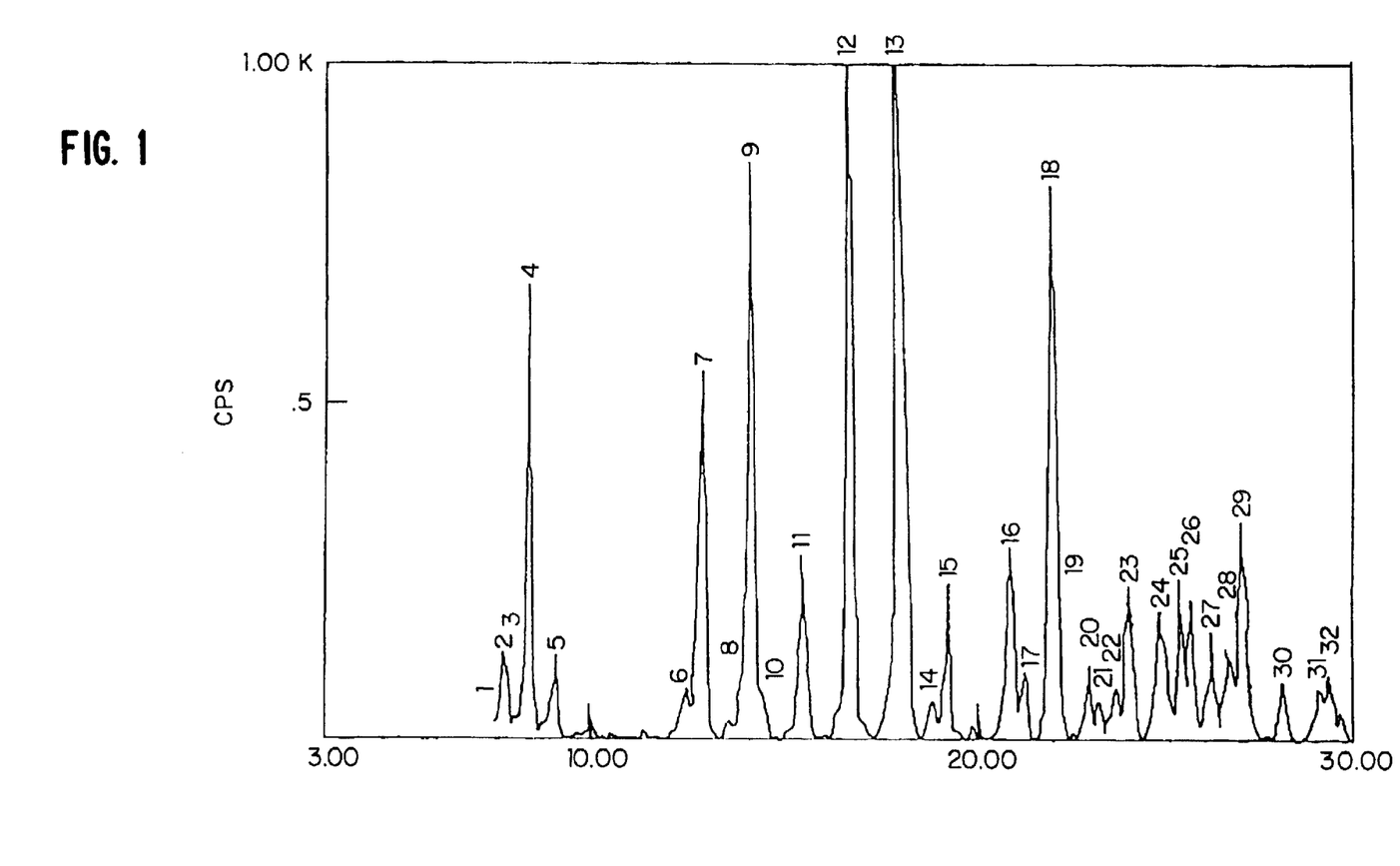
FIG. 1 represents an example of X-ray diffraction spectrum of a ³⁄₂ hydrate of the compound (I).
Figure 2:
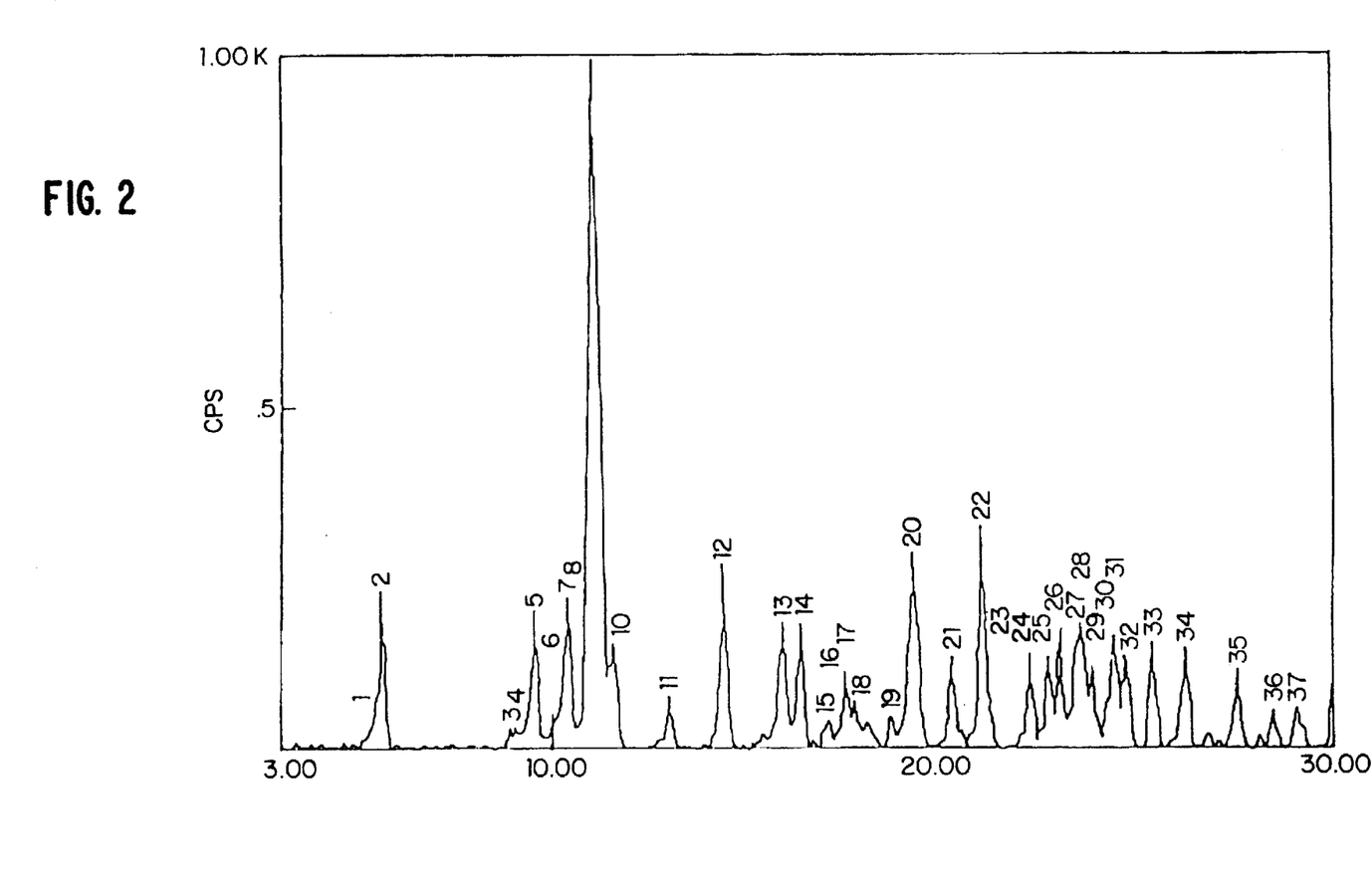
FIG. 2 represents an example of X-ray diffraction spectrum of a ½ hydrate of the compound (I).
Figure 3:
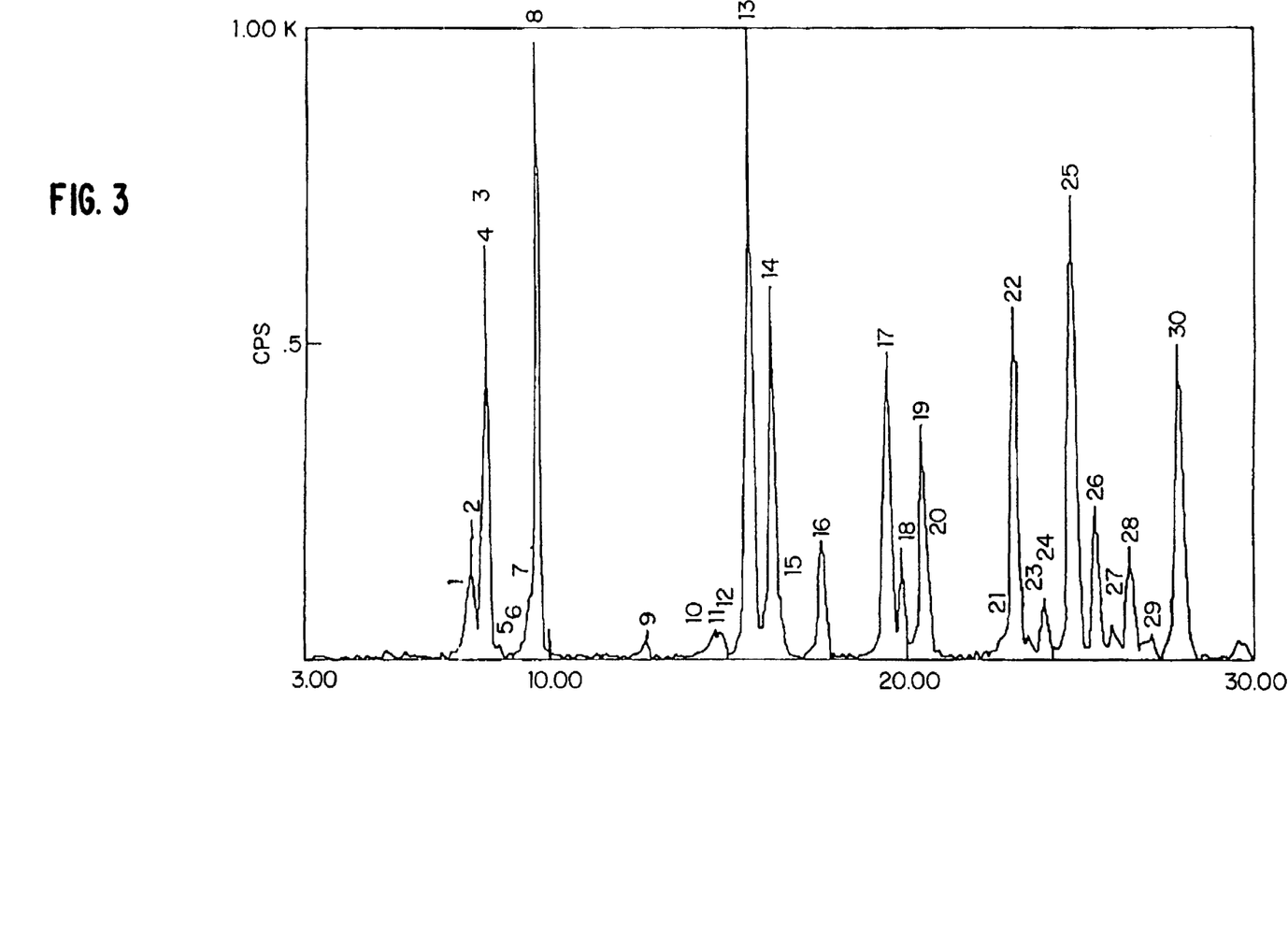
FIG. 3 represents an example of X-ray diffraction spectrum of an anhydrate of the compound (I).
Figure 4:
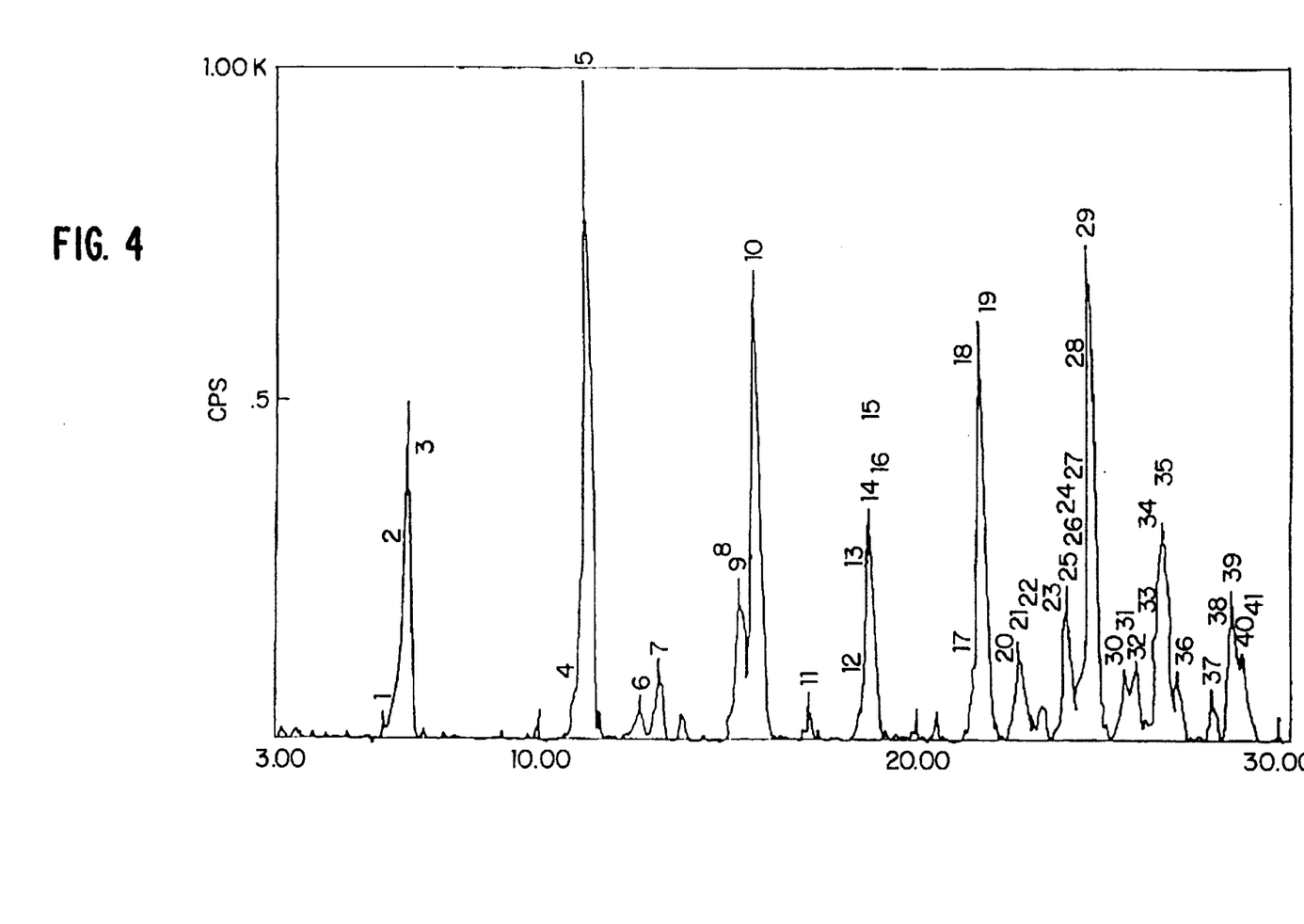
FIG. 4 represents an example of X-ray diffraction spectrum of a 1 hydrate of the compound (I).

Each of hydrates and anhydrate of compound (I) according to the present invention exhibits the spectrum pattern shown in the drawings and has the substantially characteristic pattern of the powder X-ray diffraction spectrum shown in the following Examples. The term "substantially characteristic" means that the spectrum pattern of each of the crystals is not limited to that of attached figures and tables but includes errors in lattice spacings (d values) and intensity generally accepted in this field.

It was found that more than one hydrate are formed in the crystals depending on the conditions for producing hydrate. In particular, a ½ hydrate contaminates when a ³⁄₂ hydrate is produced. Such a mixture of hydrates is unsuitable as a bulk material for pharmaceutical preparations. Thus, the inventors studied a method for selectively preparing crystals of compound (I) solely comprising a single hydrate or a single anhydrate.

The inventors examined the stability of crystals of compound (I) in an aqueous solvent or water as follows.

Equivalent amounts of a ½ hydrate and a ³⁄₂ hydrate of compound (I) were mixed, and an aqueous solvent was added to the mixture. The mixture was stirred at a varied temperature and, after a given period of time, the proportion of hydrates in the total crystals was analyzed. During the stirring, the mixture was in a suspended state, namely, a slurried state.

As for an aqueous solvent, an aqueous ethanol having a water content (hereinafter defined) between 0% to 100% was employed. It was also found that an aqueous ethanol further containing 1% of 28% aqueous ammonia increases solubility of the crystals and accelerates the conversion rate between hydrates. The solvent was used in an amount of 15 ml to 30 ml per 1 gram of the crystals. The water content of the solvent used is expressed in terms of volume ratio before mixing. For example, an aqueous ethanol having a water content of 60% means a mixture of ethanol and water at a volume ratio of 4:6, and an aqueous ethanol having a water content of 60% containing 1% aqueous ammonia is a mixture consisting of ethanol, water and 28% aqueous ammonia at a volume ratio of 40:59:1.

The stirring was continued for 3 days at a temperature of 25° C. or 45° C. The time period of 3 days is not essential for conversion of crystals, and it was proved that the conversion completes in about 1 day.

As a result of these experiments, it was proved that the kinds of crystals existing in the mixture vary depending on the temperature, the water content of the solvent, and the time.

More specifically, (i) 14-hour treatment at a refluxing temperature of the solvent gave only an anhydrate at a water content of 5% or less, only a ½ hydrate at a water content of 50%, and a mixture of a ½ hydrate and a 3/2 hydrate at a water content of 75% or more; (ii) 3-day treatment at 45° C. gave only a 3/2 hydrate at a water content of 50% or more and a mixture of a ½ hydrate and a 3/2 hydrate at a water content of 45% or less; and (iii) 3-day treatment at 25° C. gave only a 3/2 hydrate at a water content of 40% or more and a mixture of a ½ hydrate and a 3/2 hydrate at a water content of 25% or less.

It was proved from these results that a 3/2 hydrate can be obtained as a single substance by treating in a solvent having a water content of 50% or more when the temperature is 45° C.; or in a solvent having a water content of 40% or more when the temperature is 25° C.

The term "treating" as used herein means continuously stirring a mixture of crystals and a solvent in a slurried state at the aforementioned temperature for the aforementioned period.

A slurry of crystals may be prepared either by once dissolving the crystals followed by crystallization or by simply mixing the crystals and the solvent.

The solvent which can be used in the present invention is not particularly limited as long as the crystals can dissolve in the solvent and the solvent is miscible with water. Illustrative examples of the solvent include lower alcohols, such as methanol, ethanol, and propanol, and acetone, of which ethanol is preferred. In addition, water may be used solely as a solvent.

The inventors have also found that crystals consist of only a 3/2 hydrate can be prepared selectively by the recrystallization which employs as conditions at the start of crystallization the above-described conditions which allow only a 3/2 hydrate to exist in a slurried state. The term "at the start of crystallization" as used herein means the point at which all the pretreatments before formation of crystals, e.g., dissolving crude crystals in a solvent and, if desired, subjecting the solution to a treatment with activated carbon, concentration or the like, have finished.

The inventors also succeeded in establishing a method for obtaining a ½ hydrate, an anhydrate or a 1 hydrate as a single crystals by recrystallization or the treatment in a solvent by a similar manner.

For example, a 1 hydrate of compound (I) can be prepared by the treatment at about 25° C. in an aqueous methanol having a water content of 1% or less and an anhydrate can be prepared by the treatment in an ethanol containing 15% (w/w) ammonia.

The following procedures are the examples of the method for the selective preparation of the hydrates and the anhydrate of compound (I).

A) A method for the preparation of anhydrate

A mixture of the crude crystal of compound (I), which can be prepared according to the method disclosed in EP-A-0 341 493, and an aqueous methanol or an aqueous ethanol is heated under reflux with stirring in a state of slurry for from 0.5 hour to 8 hours. The water content of the aqueous methanol or ethanol is less than 5% (v/v). The amount of the solvent is in the ratio of from 10 ml to 30 ml to 1 g of the crude compound (I). Increasing the water content of the solvent tends to lessen the time for completion of the treatment. When anhydrous ethanol was employed as the solvent, the conversion completed at the temperature of 70° C. and the time of 8 hours.

The anhydrate can be obtained by the recrystallization method. One of the best procedure is exemplified as Example 3 explained later. In this procedure, an aqueous solvent containing less than 5% (v/v) of water can be employed as the solvent.

B) A method for the preparation of ½ hydrate

A mixture of the crude crystal of compound (I) and an aqueous ethanol having a water content of 50% is heated under reflux with stirring in a state of slurry for from 1 hour to 20 hours. The amount of the solvent is in the ratio of from 10 ml to 30 ml to 1 g of the crude compound (I). It was known that when the solvent containing ammonia was used the rate of the formation of ½ hydrate was accelerated.

The ½ hydrate can be obtained by the recrystallization method. One of the best procedure is exemplified as Example 2 explained later.

C) A method for the preparation of 1 hydrate

One of the best procedure for the selective preparation of 1 hydrate is exemplified as Example 4 explained later.

D) A method for the preparation of 3/2 hydrate

The 3/2 hydrate is obtained from a slurry mixture stirred under the condition previously explained under which the 3/2 hydrate predominantly forms. The condition in which the 3/2 hydrate predominantly forms is mainly determined by the water content of the solvent and the temperature, and the relation is summarized in the following table.

TABLE

| The predominant region in the slurry of 3/2 hydrate | |
|---|---|
| Temperature (°C.) | Water Content |
| 45 | more than 50% |
| 50 | more than 60% |
| 55 | more than 70% |
| 60 | more than 90% |

The amount of the solvent is in the ratio of from 10 ml to 30 ml to 1 g of the crude compound (I).

The 3/2 hydrate can be obtained by the recrystallization procedure. The preferable procedure is exemplified as Examples 1 and 5 explained later. For the recrystallization procedure, it is preferable, generally, to employ a solvent containing ammonia, because the amount of the solvent required can be decreased. The amount of the solvent is in the ratio of from 5 ml to 50 ml to 1 g of the crude compound (I), and preferably from 10 ml to 20 ml. The water content of the solvent is in the range of from 50% to 100%, and preferably from 50% to 75%. If the content of ammonia is raised, the solvent used can be decreased. The amount of ammonia is in the ratio of from 0.5 g to 2.0 g, preferably from 0.7 g to 1.0 g, to 1 g of the crude compound (I). The solvent containing ammonia can be prepared by adding ammonia water or by introducing gaseous ammonia to the solvent. When ammonia water is employed, the water ingredient thereof needs to be calculated to obtain the solvent of precise water content. The temperature for crystallization can be determined according to the table above.

The crystal of the present invention can be formulated into antimicrobial preparations in an appropriate solid preparation form by the conventional preparation methods. The solid preparation form for oral administration includes tablets, powders, granules and capsules.

In the preparation of solid preparations, the active ingredient may be mixed with appropriately selected pharmaceutically acceptable excipients, such as fillers, extenders, binders, disintegrators, dissolution accelerators, wetting agents, and lubricants.

The crystal of the invention can be formulated into preparations for animals, such as powders, fine granules, and solubilized powders by commonly employed preparation methods.

The present invention will now be illustrated in greater detail with reference to Examples, but it should be understood that the present invention is not construed as being limited thereto.

The powder X-ray diffraction spectrum data shown in the Examples were determined under the following conditions using a Geiger Flex machine manufactured by Rigaku-Denki.

| Target: | Cu—Kα |
|---|---|
| Filter: | Ni |
| Voltage: | 40 kV |
| Current: | 20 mA |

EXAMPLE 1

7-[(7-(S)-Amino-5-azaspiro[2.4]heptan-5-yl]-8-chloro-6-fluoro-1-[(1R,2S)-2-fluorocyclopropyl]-4-oxo-1,4-dihydroquinoline-3-carboxylic Acid 3/2 Hydrate Crude crystals of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid (150 g) were added to a mixture of 5500 ml of an aqueous ethanol having a water content of 75% and 450 ml of 28% aqueous ammonia, and the mixture was stirred in a water bath at 45° C. for 30 minutes. After dissolving the crystals, 7.5 g of activated carbon was added to the solution, followed by filtration. The filtrate was concentrated under reduced pressure at an outer temperature of 45° C. to remove about 3000 ml of the solvent by evaporation. The concentrate was cooled to room temperature, and the precipitated crystals were collected by filtration and dried at 40° C. under reduced pressure to yield 143 g of the title compound.

Melting Point: 225° C. (decomposition)

Powder X-Ray Diffractometry (characteristic peaks):

| d Value (lattice spacings) (Å) | Relative Intensity |
|---|---|
| 11.47 | Weak |
| 10.49 | Strong |
| 9.69 | Weak |
| 7.12 | Extremely Weak |
| 6.87 | Strong |
| 6.23 | Strong |
| 5.68 | Weak |
| 5.25 | Strong |
| 4.90 | Extremely Strong |
| 4.71 | Extremely Weak |
| 4.61 | Weak |
| 4.25 | Weak |
| 4.15 | Extremely Weak |
| 4.01 | Strong |
| 3.85 | Extremely Weak |
| 3.80 | Extremely Weak |
| 3.74 | Extremely Weak |
| 3.69 | Weak |
| 3.58 | Weak |
| 3.50 | Weak |
| 3.46 | Weak |
| 3.39 | Weak |
| 3.34 | Weak |
| 3.29 | Weak |
| 3.17 | Weak |

IR; $V_{max}$ (KBr) cm$^{-1}$: 3450, 3000, 2880, 1620

Elemental Analysis, for $C_{19}H_{18}F_2ClN_3O_3 \cdot 3/2H_2O$:

Calcd. (%): C 52.24; H 4.85; N 9.62

Found (%): C 52.07; H 4.68; N 9.47

Water Content (Karl Fischer's method):

Calcd.: 6.18%; Found: 6.5%

EXAMPLE 2

7-[(7-(S)-Amino-5-azaspiro[2.4]heptan-5-yl]-8-chloro-6-fluoro-1-[(1R,2S)-2-fluorocyclopropyl]-4-oxo-1,4-dihydroquinoline-3-carboxylic Acid ½ Hydrate Crude crystals of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid (4.0 g) were added to a mixture of 160 ml of an aqueous ethanol having a water content of 50% and 6 ml of 28% aqueous ammonia, and the mixture was stirred at 60° C. for 30 minutes. After dissolving the crystals, 0.2 g of activated carbon was added to the solution, followed by filtration. The filtrate was concentrated under atmospheric pressure to remove about 80 ml of the solvent. The concentrate was cooled to room temperature, and the precipitated crystals were collected by filtration and dried at 40° C. under reduced pressure to give 3.6 g of the title compound.

Melting Point: 195° C. (decomposition)

Powder X-Ray Diffractometry (characteristic peaks):

| d Value (lattice spacings) (Å) | Relative Intensity |
|---|---|
| 15.66 | Weak |
| 9.19 | Weak |
| 8.42 | Weak |
| 7.80 | Extremely Strong |
| 7.60 | Weak |
| 6.82 | Extremely weak |
| 6.15 | Weak |
| 5.55 | Weak |
| 5.40 | Weak |
| 4.60 | Weak |
| 4.23 | Weak |

IR; $V_{max}$ (KBr) cm$^{-1}$: 3420, 3000, 2860, 1620

Elemental Analysis, for $C_{19}H_{18}F_2ClN_3O_3 \cdot \frac{1}{2}H_2O$:

Calcd. (%): C 54.49; H 4.57; N 10.03

Found (%): C 54.59; H 4.29; N 9.88

Water Content (Karl Fischer's method):

Calcd.: 2.15%; Found: 2.1%

EXAMPLE 3

7-[(7-(S)-Amino-5-azaspiro[2.4]heptan-5-yl]-8-chloro-6-fluoro-1-[(1R,2S)-2-fluorocyclopropyl]-4-oxo-1,4-dihydroquinoline-3-carboxylic Acid Anhydrate Crude crystals of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid (4 g) were added to 360 ml of 15% ammonia-ethanol (on a weight basis; prepared by blowing ammonia gas into absolute ethanol), and the mixture was stirred for 30 minutes. After dissolving the crystals, 0.2 g of activated carbon was added to the solution, followed by filtration. The filtrate was concentrated under atmospheric pressure to remove about 260 ml of the solvent. The concentrate was cooled to room temperature, and the precipitated crystals were collected by filtration and dried at 40° C. under reduced pressure to give 3.5 g of the title compound.

Melting Point: 231° C. (decomposition)
Powder X-Ray Diffractometry (characteristic peaks):

| d Value (lattice spacings) (Å) | Relative Intensity |
|---|---|
| 11.35 | Weak |
| 10.72 | Strong |
| 9.07 | Extremely Strong |
| 6.94 | Extremely Weak |
| 5.63 | Extremely Strong |
| 5.42 | Strong |
| 4.99 | Weak |
| 4.54 | Strong |
| 4.45 | Weak |
| 4.32 | Strong |
| 3.83 | Strong |
| 3.70 | Extremely Weak |
| 3.56 | Strong |
| 3.47 | Weak |
| 3.42 | Extremely Weak |
| 3.35 | Weak |
| 3.19 | Strong |

IR; $V_{max}$ (KBr) cm$^{-1}$: 3430, 2950, 2800, 1630, 1610
Elemental Analysis, for $C_{19}H_{18}F_2ClN_3O_3$:
Calcd. (%): C 55.69; H 4.43; N 10.25
Found (%): C 55.78; H 4.23; N 10.26
Water Content (Karl Fischer's method):
Calcd.: 0%; Found: 0.2%

EXAMPLE 4

7-[(7-(S)-Amino-5-azaspiro[2.4]heptan-5-yl]-8-chloro-6-fluoro-1-[(1R,2S)-2-fluorocyclopropyl]-4-oxo-1,4-dihydroquinoline-3-carboxylic Acid Monohydrate Crude crystals of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid (5 g) were added to 150 ml of an aqueous methanol having a water content of 1% or less to form a slurry. The slurry was stirred at 25° C. for 3 days. The crystals were collected by filtration and dried at room temperature under reduced pressure until it was confirmed that the weight became constant to give 4.5 g of the title compound.

Powder X-Ray Diffractometry (characteristic peaks):

| d Value (lattice spacings) (Å) | Relative Intensity |
|---|---|
| 13.22 | Strong |
| 7.74 | Extremely Strong |
| 6.94 | Extremely Weak |
| 6.68 | Weak |
| 5.77 | Weak |
| 5.60 | Strong |
| 5.16 | Extremely Weak |
| 4.71 | Medium |
| 4.09 | Strong |
| 3.91 | Weak |
| 3.72 | Weak |
| 3.60 | Strong |

IR; $V_{max}$ (KBr) cm$^{-1}$: 3620, 3410, 3080, 2870, 1630, 1610, 1545
Elemental Analysis, for $C_{19}H_{18}F_2ClN_3O_3 \cdot H_2O$:
Calcd. (%): C 53.34; H 4.71; N 9.82
Found (%): C 53.31; H 4.55; N 9.93

Water Content (Karl Fischer's method):
Calcd.: 4.2%; Found: 4.1%

EXAMPLE 5

7-[7-(S)-Amino-5-azaspiro-[2.4]heptan-5-yl]-8-chloro-6-fluoro-1-[(1R,2S)-2-fluorocyclopropyl]-4-oxo-1,4-dihydroquinoline-3-carboxylic Acid ³⁄₂ Hydrate Crude crystals of 7-[7-(S)-amino-5-azaspiro-[2.4]heptan-5-yl]-8-chloro-6-fluoro-1-[(1R,2S)-2-fluorocyclopropyl]-4-oxo-1,4-dihydroquinoline-3-carboxylic acid(7.7 g) were added to a mixture of 45 ml of ethanol, 37 ml of water and 25 ml of 28% ammonia water, and the whole mixture was stirred on a bath of 45° C. for 10 minutes. After dissolving the crystals, about 50 ml of the solvent was removed under reduced pressure. The mixture was cooled to room temperature, and a resulting crystals were collected by filtration, then dried at 40° C. in vacuo to yield 7.3 g (94.8%) of the titled compound.

FORMULATION EXAMPLE 1

| Capsule: | |
|---|---|
| Compound of Example 1 (3/2 hydrate) | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| Total: | 150.0 mg |

FORMULATION EXAMPLE 2

| Powder for Admixture with Feedstuff: | |
|---|---|
| Compound of Example 1 (3/2 hydrate) | 1 to 10 g |
| Corn starch | 89.5 to 98.5 g |
| Light anhydrous silicic acid | 0.5 g |
| Total: | 100 g |

While the invention has been described in detail and with reference to specific examples thereof, it will be apparent to one skilled in the art that various changes and modifications can be made therein without departing from the spirit and scope thereof.

What is claimed is:

1. A method for selectively obtaining a ³⁄₂ hydrate of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid which comprises treating 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid in an aqueous solvent or recrystallizing 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid from an aqueous solvent, wherein said treating or recrystallizing is carried out for 1–3 days at a temperature of at least 25° C., and said aqueous solvent has a water content of at least 40%.

2. The method according to claim 1, wherein said treating occurs at a temperature of 45° C., and wherein the aqueous solvent has a water content of at least 50%.

3. The method according to claim 1, wherein said treating occurs at a temperature of 50° C., and wherein the aqueous solvent has a water content of at least 60%.

4. The method according to claim 1, wherein said treating occurs at a temperature of 55° C., and wherein the aqueous solvent has a water content of at least 70%.

5. The method according to claim 1, wherein said treating occurs at a temperature of 60° C., and wherein the aqueous solvent has a water content of 90%.

6. The method according to claims 1, 2, 3, 4 or 5, wherein the aqueous solvent is aqueous ethanol containing 1% of 28% aqueous ammonia.

7. The method according to claim 1, wherein the amount of the aqueous solvent employed is from 10 to 30 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

8. The method according to claim 6, wherein said recrystallizing employs an aqueous solvent containing 0.5–2.0 g of ammonia per 1.0 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid, and the aqueous solvent is employed in an amount of from 5 ml to 50 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

9. The method of claim 8, wherein the aqueous solvent contains 0.7–1.0 g of ammonia per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid, and the aqueous solvent is employed in an amount of from 10 ml to 20 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

10. The method of claim 8, wherein the water content is in the range of from 50% to 100%.

11. The method of claim 10, wherein the water content is in the range of from 50% to 75%.

12. 7-[(7-(S)-Amino -5azaspiro[2.4]heptan-5-yl]-8-chloro-6-fluoro-1-[(1R,2S)-2fluorocyclopropyl]-4-oxo-1,4-dihydroquinoline-3-carboxylic acid anhydrate.

13. A method for selectively obtaining a ½ hydrate of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid which comprises treating 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid in an aqueous solvent, wherein said treating is carried out for 1–3 days at a temperature of at least 25° C., and said aqueous solvent has a water content of at least 40%.

14. The method according to claim 13, wherein said treating occurs at a temperature of 45° C., and wherein the aqueous solvent has a water content of at least 50%.

15. The method according to claim 13, wherein said treating occurs at a temperature of 50° C., and wherein the aqueous solvent has a water content of at least 60%.

16. The method according to claim 13, wherein said treating occurs at a temperature of 55° C., and wherein the aqueous solvent has a water content of at least 70%.

17. The method according to claim 13, wherein said treating occurs at a temperature of 60° C., and wherein the aqueous solvent has a water content of 90%.

18. The method according to claims 13, 14, 15, 16 or 17, wherein the aqueous solvent is aqueous ethanol containing 1% of 28% aqueous ammonia.

19. The method according to claim 13, wherein the amount of the aqueous solvent employed is from 10 to 30 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

20. A method for selectively obtaining a ½ hydrate of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid which comprises recrystallizing 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid from an aqueous solvent, wherein at the start of said recrystallizing said temperature is at least 25° C., and said aqueous solvent has a water content of at least 40%.

21. The method according to claim 20, wherein at the start of said recrystallizing, said temperature is 45° C., and said aqueous solvent has a water content of at least 50%.

22. The method according to claim 20, wherein at the start of said recrystallizing, said temperature is 50° C., and said aqueous solvent has a water content of at least 60%.

23. The method according to claim 20, wherein at the start of said recrystallizing, said temperature is 55° C., and said aqueous solvent has a water content of at least 70%.

24. The method according to claim 20, wherein at the start of said recrystallizing, said temperature is 60° C., and said aqueous solvent has a water content of 90%.

25. The method according to claims 20, 21, 22, 23 or 24, wherein the aqueous solvent is aqueous ethanol containing 1% of 28% aqueous ammonia.

26. The method according to claim 20, wherein the amount of the aqueous solvent employed is from 10 to 30 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

27. The method according to claim 20, wherein said recrystallizing employs an aqueous solvent contains 0.5–2.0 g of ammonia per 1.0 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid, and the aqueous solvent is employed in an amount of from 5 ml to 50 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

28. The method of claim 27, wherein the aqueous solvent contains amino-0.7–1.0 g of ammonia per amino-1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid, and the aqueous solvent is employed in an amount of from 10 ml to 20 ml per 1 g of 7-[(7-5)-amino-5-azaspiro[2.4]heptan-5-yl]-8-chloro-6-fluoro-1-[(1R,2S)-2-fluorocyclopropyl]-4-oxo-1,4-dihydroquinoline-3-carboxylic acid.

29. The method of claim 27, wherein the water content is in the range of from 50% to 100%.

30. The method of claim 28, wherein the water content is in the range of from 50% to 75%.

31. A crystal of 7-[(7-(S)-amino-5-azaspiro[2.4]heptan-5-yl]-8-chloro-6-fluoro-1-[(1R,2S)-2-fluorocyclopropyl]-4-oxo-1,4-dihydroquinoline- 3-carboxylic acid anhydrate which has substantially the following X-ray diffraction characteristics:

| d Value (lattice spacings) (Å) | Relative Intensity |
| --- | --- |
| 11.35 | Weak |
| 10.72 | Strong |

| d Value (lattice spacings) (Å) | Relative Intensity |
|---|---|
| 9.07 | Extremely Strong |
| 6.94 | Extremely Weak |
| 5.63 | Extremely Strong |
| 5.42 | Strong |
| 4.99 | Weak |
| 4.54 | Strong |
| 4.45 | Weak |
| 4.32 | Strong |
| 3.83 | Strong |
| 3.70 | Extremely Weak |

| d Value (lattice spacings) (Å) | Relative Intensity |
|---|---|
| 3.56 | Strong |
| 3.47 | Weak |
| 3.42 | Extremely Weak |
| 3.35 | Weak |
| 3.19 | Strong. |

\* \* \* \* \*